United States Patent
Lindemann (10) Patent No.: US 9,632,080 B2
(45) Date of Patent: Apr. 25, 2017

(54) DIAGNOSTIC MULTI-LAYER DRY PHASE TEST STRIP WITH INTEGRATED BIOSENSORS ("ELECTROSTRIP")

(75) Inventor: Björn F. Lindemann, Hamburg (DE)

(73) Assignee: Polymer Technology Systems, Inc., Indianapolis, IN (US)

( * ) Notice: Subject to any disclaimer, the term of this patent is extended or adjusted under 35 U.S.C. 154(b) by 1101 days.

(21) Appl. No.: 13/146,169

(22) PCT Filed: Jun. 11, 2009

(86) PCT No.: PCT/US2009/047106
§ 371 (c)(1),
(2), (4) Date: Oct. 18, 2011

(87) PCT Pub. No.: WO2010/085271
PCT Pub. Date: Jul. 29, 2010

(65) Prior Publication Data
US 2012/0037513 A1    Feb. 16, 2012

Related U.S. Application Data (60) Provisional application No. 61/147,001, filed on Jan. 23, 2009.

(51) Int. Cl.
*G01N 27/403* (2006.01)
*G01N 33/487* (2006.01)
(Continued)

(52) U.S. Cl.
CPC ....... *G01N 33/54386* (2013.01); *C12Q 1/001* (2013.01); *G01N 27/3272* (2013.01)

(58) Field of Classification Search
CPC .................. C12Q 1/00–1/001; C12Q 1/006
(Continued)

(56) References Cited

U.S. PATENT DOCUMENTS

| 5,140,985 A | 8/1992 | Schroeder et al. |
| 5,213,964 A | 5/1993 | Jones |

(Continued)

FOREIGN PATENT DOCUMENTS

| CN | 2372689 Y | 4/2000 |
| CN | 1309294 A | 8/2001 |

(Continued)

OTHER PUBLICATIONS

Search Report in co-pending Chinese Patent Application No. 200980156888.5 dated Aug. 15, 2013, 2 pages.

(Continued)

*Primary Examiner* — Gurpreet Kaur
(74) *Attorney, Agent, or Firm* — Haynes and Boone, LLP (57) ABSTRACT

A diagnostic multi-layer dry phase test strip with integrated biosensors for use in measuring more than one analyte in a fluid sample includes a body having a port for introducing a fluid sample. Within the body is a spreader layer configured to evenly spread the fluid sample received through the port. The test strip further includes at least one enzyme reaction layer in fluidic communication with the spreader layer. The test strip also includes a first electrode layer in fluidic communication with the at least one enzyme reaction layer. The first electrode layer includes a set of electrodes for each of the at least one enzyme reaction layer. Each set of electrodes is capable of electrically interacting with the fluid sample.

20 Claims, 9 Drawing Sheets (51) Int. Cl.
*C12Q 1/00* (2006.01)
*G01N 33/543* (2006.01)
*G01N 27/327* (2006.01)

(58) Field of Classification Search
USPC .... 204/403.01–403.15; 205/777.5, 778, 792; 600/345–348; 435/4–40.52; 436/62–71, 436/500–548
See application file for complete search history.

(56) References Cited

U.S. PATENT DOCUMENTS

| | | |
|---|---|---|
| 5,213,965 A | 5/1993 | Jones |
| 5,312,590 A * | 5/1994 | Gunasingham ............ 204/403.1 |
| 5,316,916 A | 5/1994 | Jones |
| 5,426,030 A | 6/1995 | Rittersdorf et al. |
| 5,451,370 A | 9/1995 | Jones |
| 5,580,743 A | 12/1996 | Rittersdorf et al. |
| 5,786,164 A | 7/1998 | Rittersdorf et al. |
| 6,171,849 B1 | 1/2001 | Rittersdorf et al. |
| 6,214,570 B1 | 4/2001 | Rittersdorf et al. |
| 7,087,397 B2 | 8/2006 | Anaokar et al. |
| 7,374,719 B2 | 5/2008 | Anaokar et al. |
| 7,494,818 B1 | 2/2009 | Anaokar et al. |
| 2003/0031698 A1* | 2/2003 | Roeder et al. ................ 424/423 |
| 2003/0068666 A1* | 4/2003 | Zweig ............................. 435/14 |
| 2005/0003523 A1 | 1/2005 | Anaokar et al. |
| 2006/0175205 A1* | 8/2006 | Cui et al. ................... 205/777.5 |
| 2009/0071846 A1* | 3/2009 | Staib et al. ................ 205/777.5 |
| 2011/0155590 A1* | 6/2011 | Huffstodt et al. ............ 205/792 |

FOREIGN PATENT DOCUMENTS

| | | |
|---|---|---|
| CN | 1337005 A | 2/2002 |
| CN | 101413941 A | 4/2009 |
| WO | WO-02063296 A1 | 8/2002 |

OTHER PUBLICATIONS

Office Action issued in co-pending European Application No. 09789795.3 dated Feb. 18, 2016 (5 pages).

* cited by examiner

DIAGNOSTIC MULTI-LAYER DRY PHASE TEST STRIP WITH INTEGRATED BIOSENSORS ("ELECTROSTRIP")

CROSS-REFERENCE TO RELATED APPLICATIONS

This application is a national stage of PCT Patent Application No. PCT/US09/47106 filed Jun. 11, 2009, which claims the benefit of U.S. Provisional Patent Application No. 61/147,001 filed Jan. 23, 2009. The foregoing PCT and provisional applications are hereby incorporated by reference to the same extent as though fully disclosed herein.

BACKGROUND OF THE INVENTION

Electrochemical test strips are widely used in blood glucose meters and have been shown to have an improved performance (shorter measurement times, higher reproducibility, increased accuracy) and improved patient compliance (less sample volume) compared to optical readout methods.

However, so far it has been impossible to measure more than a single parameter on one test strip without having to separate the strip into several independent electrochemical "cells"—one for each parameter. In these setups, a separate sample has to be added to each "cell" leading to discrepancies in sample composition, increased handling time and effort, and low patient compliance, because the patient has to give several blood samples.

BRIEF SUMMARY OF THE INVENTION

In one embodiment, a diagnostic multi-layer dry phase test strip with integrated biosensors for use in measuring more than one analyte in a fluid sample includes a body having a port for introducing a fluid sample. Within the body is a spreader layer configured to evenly spread the fluid sample received through the port. The test strip further includes at least one enzyme reaction layer in fluidic communication with the spreader layer. The test strip also includes a first electrode layer in fluidic communication with the at least one enzyme reaction layer. The first electrode layer includes a set of electrodes for each of the at least one enzyme reaction layer. Each set of electrodes is capable of electrically interacting with the fluid sample.

In one alternative, the diagnostic multi-layer dry phase test strip has at least two enzyme reaction layers. In another alternative, the diagnostic multi-layer dry phase test strip includes an electrically insulating base layer, a plurality of lead terminals formed on the base layer, and a plurality of lead wires connected to the lead terminals, respectively, wherein each set of electrodes includes at least one working electrode, at least one counter-electrode, and at least one reference electrode connected to the lead wires, respectively.

In another alternative, the diagnostic multi-layer dry phase test strip includes a second electrode layer formed on top of the enzyme reaction layer. The electrode layer carries a plurality of lead terminals formed on the layer, a plurality of lead wires connected to the lead terminals, respectively, and an additional set of electrodes corresponding to each set of electrodes, each additional set of electrodes connected to the lead wires, respectively. In yet another alternative, the electrically conducting surface of the second electrode layer is facing downward and is in fluidic communication with the enzyme reaction layer. In another alternative, the electrically conducting surface of the second electrode layer is facing upward and is in fluidic communication with the enzyme reaction layer. In another alternative, the second electrode layer has at least one opening. Optionally, the openings are approximately centered in the electrodes of the second electrode layer. Additionally, the electrodes of the second electrode layer may be circular.

In another alternative, the diagnostic multi-layer dry phase test strip has at least one additional functional layer which is formed between the at least two enzyme reaction layers and the spreader layer. The additional functional layer may be a blood separation layer. The additional functional layer may be a precipitation layer. The additional layer may be a spacer layer or blank layer.

In one alternative, the carrier base has at least one window enabling the test strip to be optically observed. The window may be positioned opposite the port.

In another alternative, the electrically insulating base layer is transparent. Further, the enzyme reaction layer may contain chemicals for an electrochemical quantification of the enzyme reaction. Optionally, the enzyme reaction layer contains chemicals for an electrochemical reaction and an optical quantification of the enzyme reaction. Further, the electrochemical reaction and an optical quantification may occur simultaneously.

In yet another alternative, the diagnostic multi-layer dry phase test strip has a number of electrode sets between 2 and 100. In one alternative, at least one of the sets of electrodes is used as a reference set of electrodes/cells. Optionally, at least one of the sets of electrodes has the same test characteristics as another set of electrodes.

In one alternative of the diagnostic multi-layer dry phase test strip, a mediator is used. The mediator used may be ferrocene ($Fe(C_5H_5)_2$). The mediator used may be a ruthenium complex. In another alternative, the working electrode/electrodes contain $Fe_3O_4$ as a catalyst to eliminate the need for a mediator. In another alternative a diagnostic multi-layer dry phase test strip the set of electrodes corresponding to each of at least two enzyme reaction layers include a first and a second set of electrodes, the first set of electrodes have a first set anode and a first set cathode and the second set of electrodes have a second set anode and a second set cathode. In yet another alternative, a first resistance between the first set anode and the second set cathode is determined and a second resistance between the first set anode and the first set cathode is determined and the first resistance is subtracted from the second resistance to determine a non-cross talk resistance.

In another embodiment a method of determining more than one analyte in a fluid sample includes using a test strip comprising a body having a port for introducing a fluid sample; a spreader layer configured to evenly spread the fluid sample received through the port; at least one enzyme reaction layer in fluidic communication with the spreader layer; and a first electrode layer in fluidic communication with the at two one enzyme reaction layer, the first electrode layer including a set of electrodes for each of the at two one enzyme reaction layer, each set of electrodes capable of electrically interacting with the fluid sample, wherein the set of electrodes corresponding to each of at least two enzyme reaction layers include a first and a second set of electrodes, the first set of electrodes have a first set anode and a first set cathode and the second set of electrodes have a second set anode and a second set cathode. The method further includes measuring a first resistance between the first set anode and the second set cathode. The method further includes measuring a second resistance between the first set anode and the first set cathode. The method further includes subtracting the first resistance from the second resistance to determine a non-cross talk resistance. The method further includes determining the concentration of an analyte based on the non-cross talk resistance.

In another embodiment of a diagnostic multi-layer dry phase test strip with integrated biosensors for use in measuring more than one analyte in a fluid sample, the test strip includes a body having a port for introducing a fluid sample, a spreader layer for spreading the fluid sample received through the port, and an electrode layer in fluidic communication with the spreader layer, the first electrode layer including a first set of electrodes capable of electrically interacting with the fluid sample. In one alternative, the test strip also includes a second set of electrodes capable of electrically interacting with the fluid sample in fluidic communication with the spreader layer. Furthermore, the spreader layer may evenly distribute the sample between the first and second set of electrodes.

In one embodiment of a method of ensuring accuracy of analyte testing using a single test strip, the method includes testing a fluid sample provided on a single test strip configured to provide two tests for an analyte, determining a first and second test result with a meter configured to receive the single test strip, comparing the first and second test result using the meter, and returning a notification to the user from the meter if the results of the comparing is not within an acceptable error range. Alternatively, the two tests may be electrochemical and photometric. In one alternative, the two tests may be identical in respect to methodology and reagents. In another alternative, the two tests may have different reagents and calibration curves.

DETAILED DESCRIPTION OF THE INVENTION

In one embodiment of a diagnostic multi-layer dry phase test strip, the test strip combines the approved and well-established dry chemistry strip technology of Polymer Technology Systems, Inc. ("PTS") with additional electrode layers and an electrochemical reaction instead of a chromogenic enzyme reaction. See, for example, U.S. Pat. No. 7,374,719 and U.S. patent application Ser. No. 10/334,043, which are hereby incorporated by reference.

The PTS layer technology with a spreader layer on top of a stack that evenly distributes the sample horizontally before it penetrates into the underlying separation and precipitation layers to finally reach the undermost enzyme reaction layer is also able to distribute the sample into electrochemical cells instead of chromogenic pads. This embodiment is referred to as a multi-layer dry test strip.

Continuing with the multi-layer dry test strip example, the windows in the base plate of the strip housing are either entirely omitted or left in place for a combined readout (see below). The sample is horizontally distributed across the enzyme reaction layers by the spreader layer as the top layer of the stack. Blood cells may not have to be withheld/removed by a blood separation layer since their color (hemolysis) does not interfere with an electrochemical readout. Thus, this layer might be omitted. A spacer and/or a precipitation/isolation layer, such as for direct LDL measurements, may be added between the spreader layer and the enzyme reaction layer. Preferably at the lower end of the stack, the enzyme reaction layer holds the enzyme cocktails for the electrochemical reaction or for a combination of electrochemical and optical readout, preferably reflectance spectroscopy. Finally, at the bottom a preferably transparent base layer—e.g., a polypropylene foil—is located that carries the electrode sets. An electrode set, which may be referred to as a "cell" or "biosensor", comprises at least one working electrode, one counter-electrode, and one reference electrode as in, for example, modern blood glucometers. A plurality of such cells may be placed on the base layer, all of which are supplied with a sample through the spreader layer, thus enabling the hitherto impossible measurement of several parameters on one biosensor strip.

It has turned out that the preferred potential levels for a reliable electrochemical measurement should be higher than 700 mV. This leads to an unwanted breakdown of components in the biological sample, particularly if the sample is whole blood. These components have been shown to interfere with the measurement, thus decreasing accuracy and reproducibility. Therefore, in commercial biosensors, a so-called mediator is added to the redox reaction to lower the required potential. The mediator, for example, can be the organometallic compound ferrocene ($Fe(C_5H_5)_2$).

Recently, it was shown that a mediator can be omitted if a catalyst is added instead that facilitates the reduction of hydrogen peroxide which is formed in the cholesterol oxidase enzyme reaction. $Fe_3O_4$ ("magnetite"), a relatively inexpensive and easy-to-handle catalyst that mediates the electron transfer between electrodes and hydrogen peroxide, preferably is added to the graphite ink used to screen print the working electrode on the electrode layer.

A second electrode-carrying layer can be added on top of the enzyme reaction layer to increase the volume of the reaction compartment that is subjected to electrochemical readout. This layer preferably has openings, preferably round holes with the electrodes arranged as rings around these holes to enable a flow-through of sample into the enzyme reaction layer.

In the embodiments described below, the test strip may have a variety of electrochemical or photometric testing sites. These sites may be combined or separated by virtue of a transparent base layer for the electrodes. Further, the testing methods may occur simultaneously, or approximately so. Furthermore, since providing multiple tests are possible in a single test strip, redundancy may be built into the test strip to improve accuracy. This redundancy may be in the form of multiple tests for the same analyte using the same technique, preferably electrochemical. The redundancy may include testing for the same analyte according to different techniques: electrochemical and optical. Furthermore, two electrochemical tests may be done with different concentrations of reagents, analyzed according to different calibration curves. By using multiple tests of the same type or slightly modified tests, errors in testing can be more easily detected. Although redundancy can be incorporated in the testing of any analyte, in the case of glucose, testing errors can have serious consequences, so such redundancy may be highly desirable.

Figure 1:
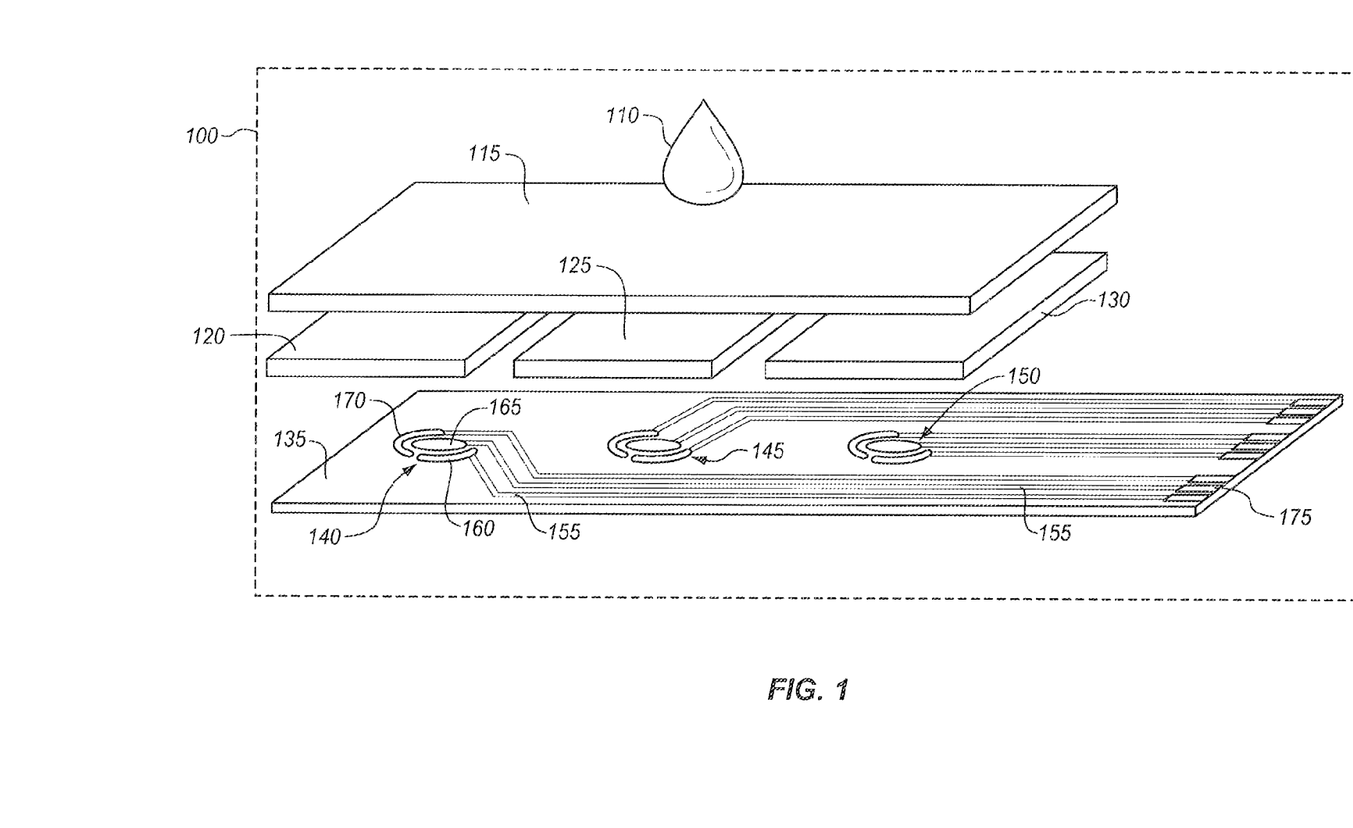
FIG. 1 is an illustration of one embodiment of a multi-layer dry phase test strip.

FIG. 1 shows one embodiment of a multi-layer dry phase test strip 100. A fluid sample 110 is applied to distribution layer 115. In this embodiment, fluid sample 110 is a blood sample; however, a variety of different bodily fluids may be tested. Distribution layer 115 functions to spread the sample evenly throughout the layer prior to transmitting the sample to the stacks 120, 125, 130. The stacks 120, 125, 130 contain reagents for reacting with the sample and isolating the analyte desired to be measured. Electrode layer 135 includes three test sites 140, 145, 150 for testing for various analytes.

Electrode layer 135 is made of a polypropylene carrier foil which can be printed on using inks adapted for such material. All three test sites 140, 145, 150 are printed in a similar fashion. The circuit paths 155 preferably are printed using carbon ink. The reference electrode 160 preferably is printed using silver/silver chloride paste. The working electrode 165 preferably is printed using carbon ink and $Fe_3O_4$. Counter-electrode 170 preferably is printed using carbon ink. In alternative embodiments, the electrodes may be composed of other materials. The circuit paths 155 end at contact leads 175 that are designed to fit into and contact the testing device providing current and measurement for use with the strip 100.

A variety of analytes may be tested using test strip 100; however, as will be explained below, various modifications can be made to test for additional analytes and to improve test characteristics. In one alternative, it is possible to eliminate the stacks 120, 125, 130 and provide for spreading from the distribution layer 115 to the three test sites 140, 145, 150. The three test sites 140, 145, 150 may be impregnated with the needed reagents.

Figure 2:
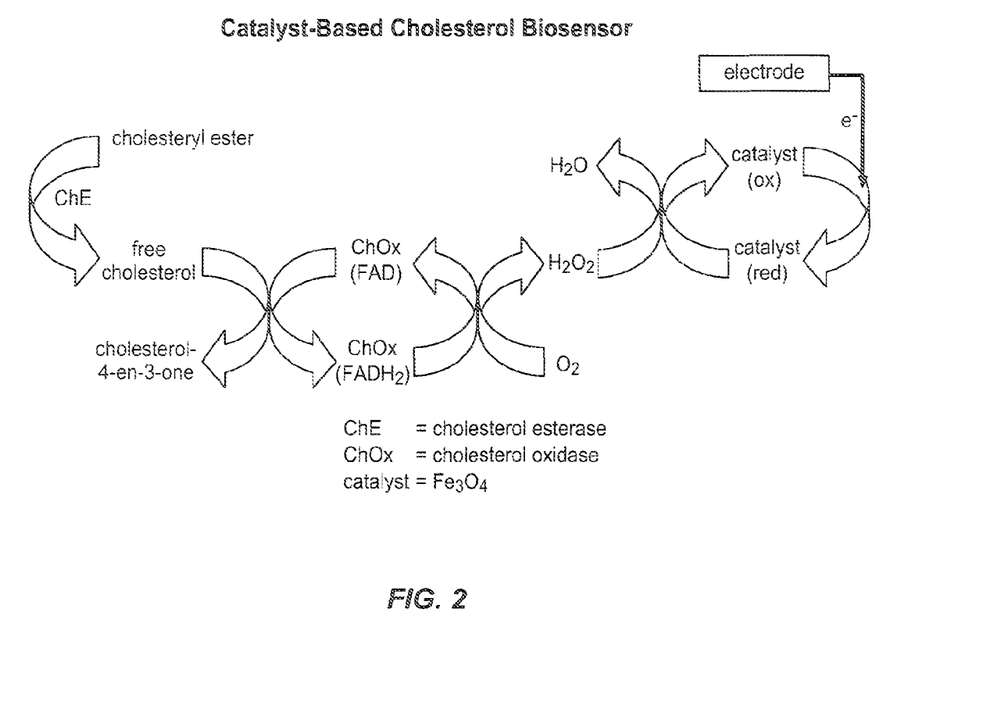
FIG. 2 is a reaction flow diagram for an embodiment of a multi-layer dry phase test strip.

FIG. 2 shows the basic reaction process for analyzing the amount of analyte. The reaction and detection is based on forming hydrogen peroxide during catalyzed reactions. The reactions are as follows:

Cholesteryl Esters+$H_2O$ - - - cholesterol esterase→cholesterol+fatty acids

Cholesterol+$O_2$ - - - cholesterol oxidase→chlesterol-4-en-3-one+$H_2O$

Figure 3:
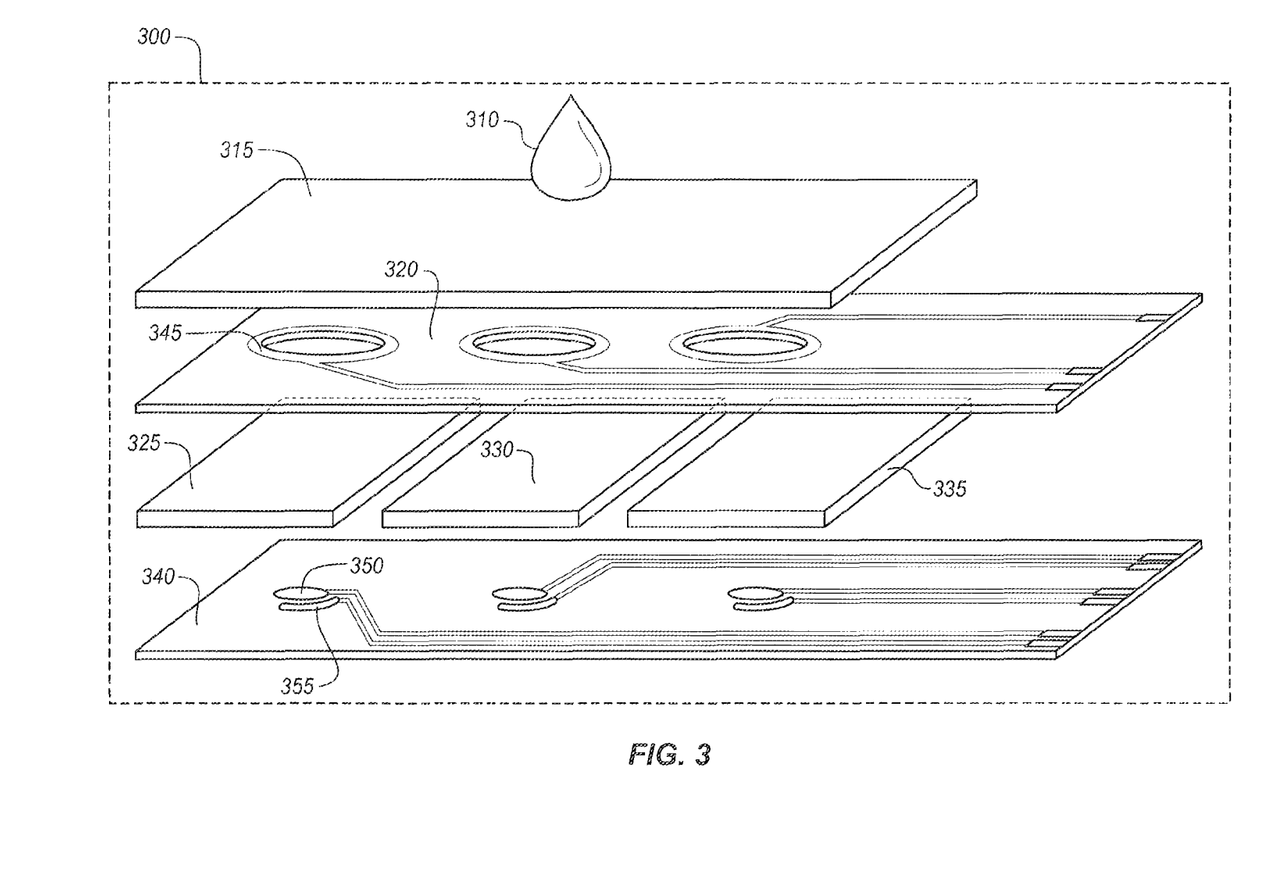
FIG. 3 is an illustration of another embodiment of a multi-layer dry phase test strip.

FIG. 3 shows an alternative embodiment for the test strip. Test strip 300 includes a separation layer 315, a first electrode layer 320, stacks 325, 330, and 335, and second electrode layer 340. In this embodiment, the counter-electrode 345 is in the first electrode layer 320, separated by a corresponding one of the stacks 325, 330, 335 from the working electrode 350 and the reference electrode 355 in second electrode layer 340. In this embodiment, counter-electrode 345 is positioned in a downward facing fashion, while working electrode 350 is positioned in an upward facing fashion. In this way, the entire volume absorbed in the stacks 325, 330, and 335 may be utilized as a sample for the purpose of electrochemical analysis. This decreases the sample volume needed for testing.

Figure 3A:
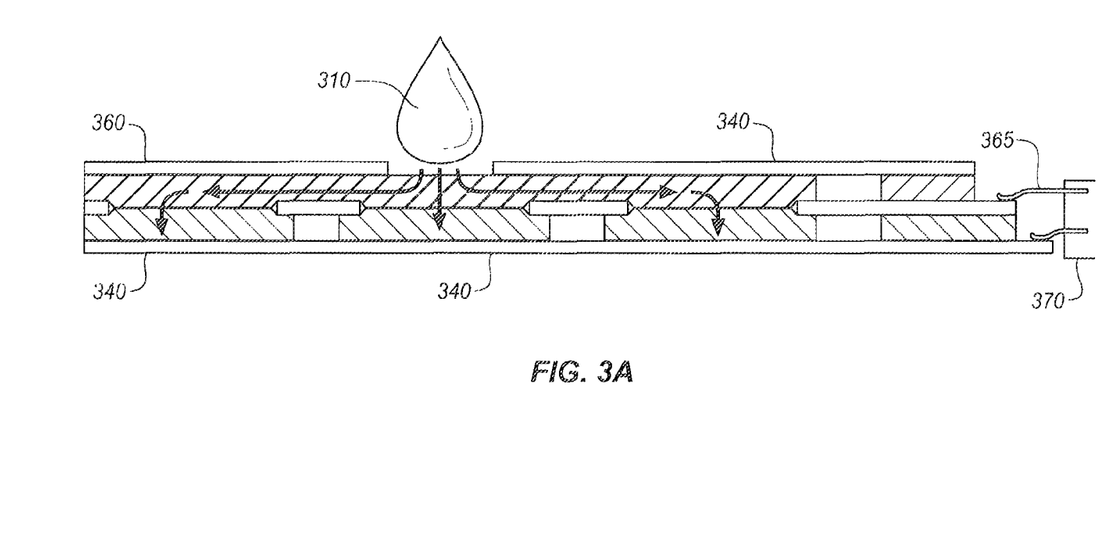
FIG. 3a is a cross-section of a multi-layer dry phase test strip according to FIG. 3.

FIG. 3a shows a side view of test strip 300 situated within a test strip holder 360. The arrows depict the flow path of sample 310 in the multi-layer test strip 300. Also shown are the leads 365 that touch the contact points of the electrodes.

The leads 365 are situated in a testing device 370, and removably touch the test strip 300, so that the test strip may be disposed of after usage.

Figure 3B:
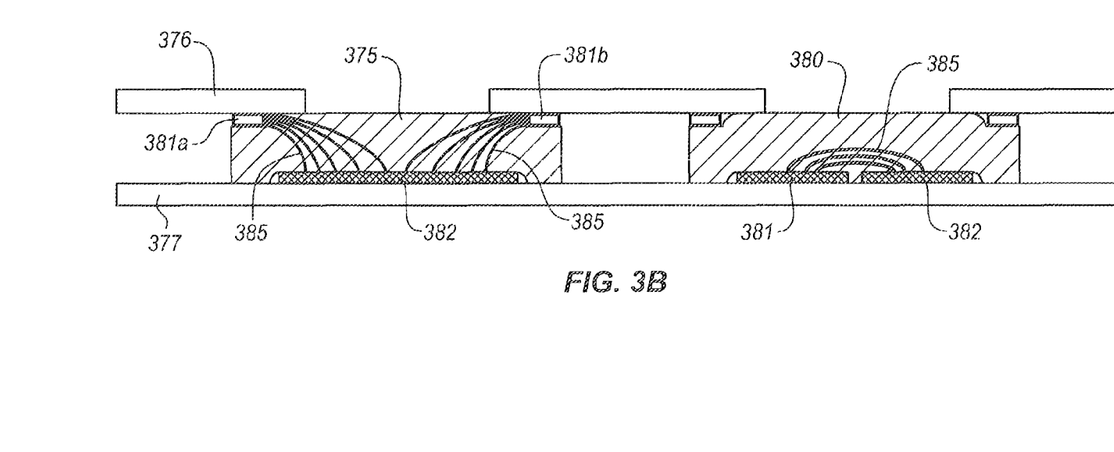
FIG. 3b is a cross-section of a multi-layer dry phase test strip showing two electrode configurations.

In FIG. 3b, a depiction of the greater test volume provided by a double electrode layer stack is shown. The entire volume of stack 375 is utilized in the double electrode layer configuration as compared to stack 380 in which the electrodes 381, 382 are side by side, resulting in only a small part of the volume being utilized. By disposing the electrodes, 381a, 381b and 382 on opposing surfaces of the stack 376, 377, a larger test volume may be utilized. As can be seen, the electrical field 385 (merely a graphical representation) travels through a greater test volume in stack 375 as compared to stack 380.

Figure 4:
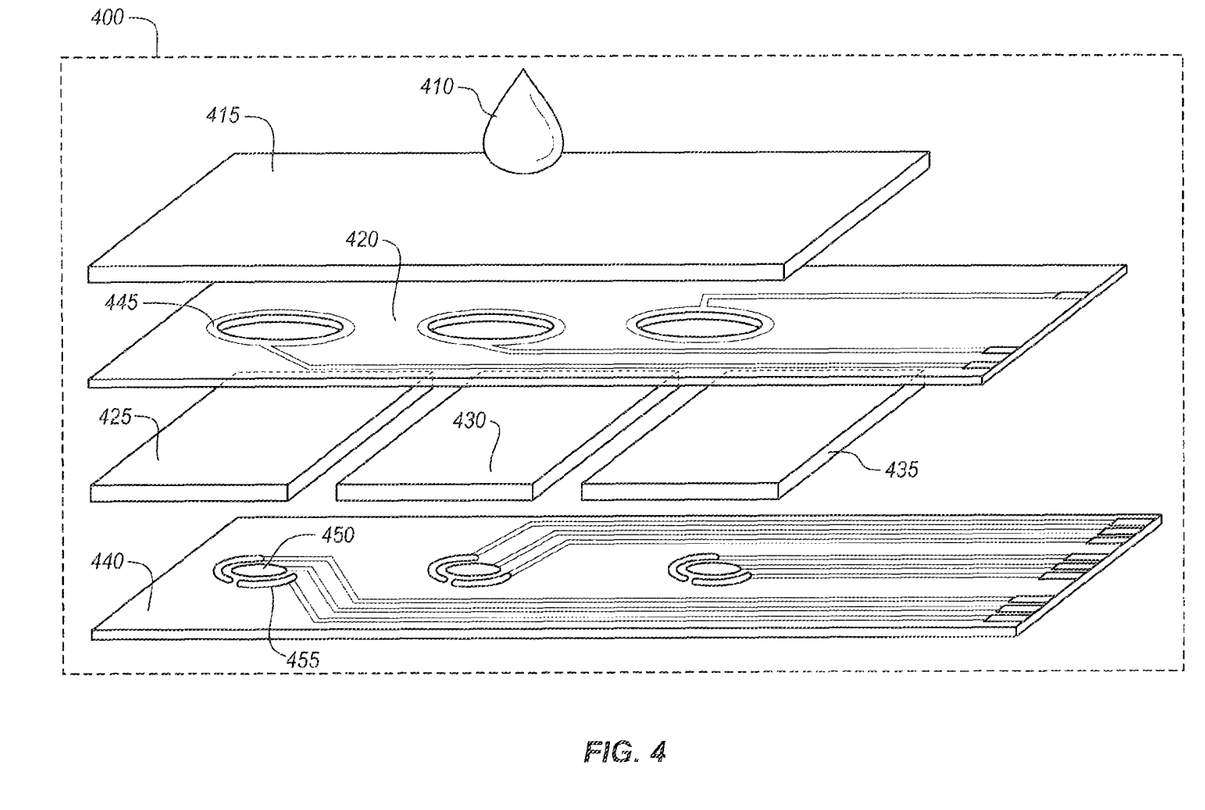
FIG. 4 is an illustration of another embodiment of a multi-layer dry phase test strip.

Another alternative embodiment shown in FIG. 4 also utilizes the entire stack volume. Test strip 400 includes a separation layer 415, a first electrode layer 420, stacks 425, 430, and 435, and second electrode layer 440. In this embodiment, the counter-electrode 445 is in the first electrode layer 420, separated by a corresponding one of the stacks 425, 430, 435 from the working electrode 450 and the reference electrode 455 in second electrode layer 440. In contrast to the embodiment of FIG. 3, the counter-electrode 445 is positioned in an upward facing fashion. The sample volume contained in stacks 425, 430, 435 preferably is sufficient to wet the counter-electrode layer 420, such that the sample touches counter-electrode 445. The upward positioning of the counter-electrode may allow for easier connection of the contact leads into a monitoring device.

Figure 5:
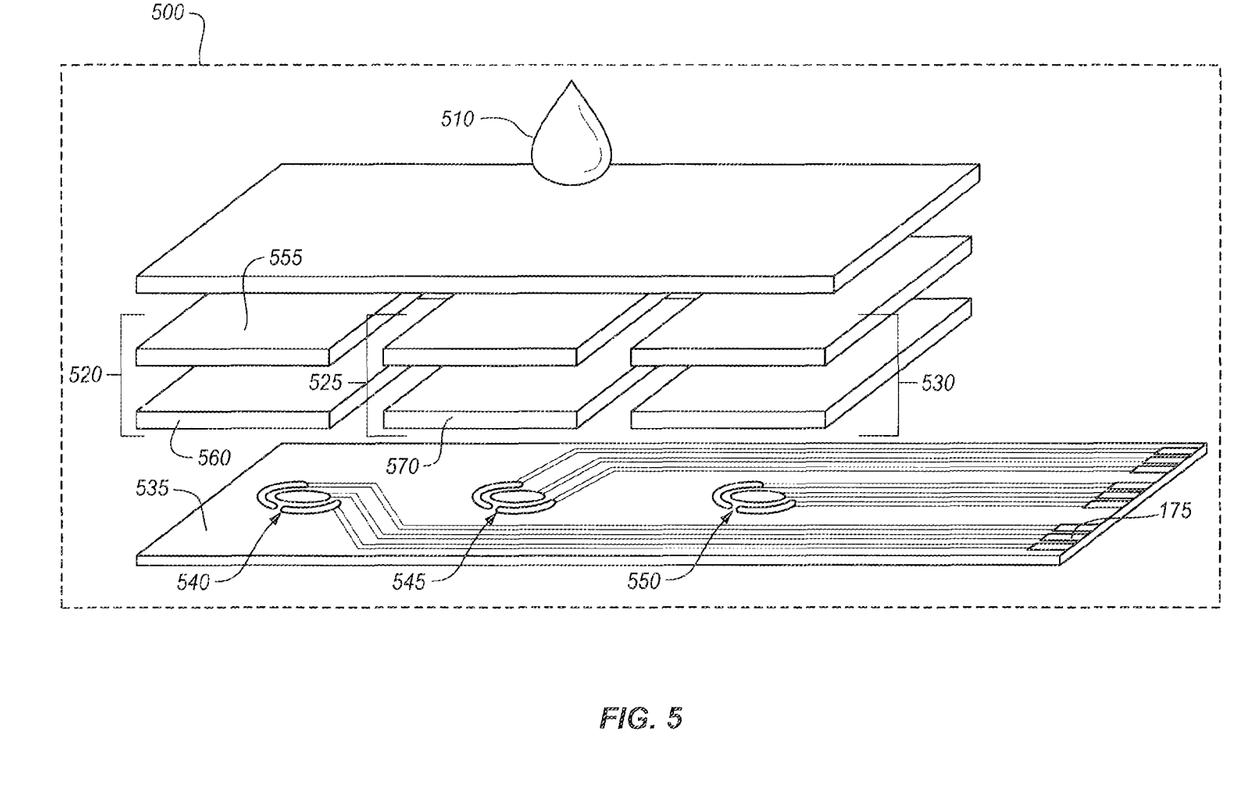
FIG. 5 is an illustration of another embodiment of a multi-layer dry phase test strip.

In FIG. 5, an alternative embodiment of the test strip is shown. Test strip 500 includes a distribution layer 515. Distribution layer 515 functions to spread the sample evenly throughout the layer prior to transmitting the sample to stacks 520, 525, and 530. Also note that an additional blood separation layer (not shown) may be included between distribution layer 515 and the stacks 520, 525, 530 for filtering red blood cells. This blood separation layer may be included in this embodiment or any of the embodiments described herein. Electrode layer 535 includes three test sites 540, 545, 550 for testing for various analytes. The stacks 525, 530, and 535 may contain one or more reaction layers and may contain one or no blank layers. Depending on the analyte measured, the stacks 525, 530, and 535 may contain one or more reaction layers and one or no blank layers. For example, stack 525 includes blank layer 555 and reaction layer 560. Blank layer 555 functions to keep the pressure on the stacks consistent between stacks and also keeps the timing of the flow consistent between stacks so that the sample reaches reaction layer 560 at the same time it reaches the reaction levels of the other stacks. In stack 530, the stack includes a precipitation layer 565 and a reaction layer 570. In the case of certain analytes, the separation of analytes in the sample is needed before reaction. For instance, an HDL measurement stack may be included in the test strip 500, requiring the usage of a precipitation layer or an isolation layer. In a precipitation layer, the analytes that are to be excluded from the reaction are precipitated out. In an isolation layer, the analytes that are to be excluded from the reaction are isolated from the analyte that is to be included in the reaction. In the case of a test strip for HDL, triglycerides, and total cholesterol, the stacks may be described as follows.

HDL Measurement Stack

With reference to FIG. 5, stack 525 is adjacent to and in fluid communication with the bottom side of distribution layer 515. Stack 525 takes fluid from distribution layer 530 and produces hydrogen peroxide in proportion to the concentration of HDL cholesterol.

As noted above, the prior art generally teaches that two layers and two associated process steps are necessary to precipitate and separate non-HDLs from plasma. According to the prior art approach, precipitation of non-HDLs is carried out in the first layer; and the precipitants then pass through this first layer to a second layer. In the second layer, the precipitants' migration is slower than that of plasma; and the plasma reaches the test membrane before the precipitant. See, e.g., U.S. Pat. Nos. 5,426,030; 5,580,743; 5,786,164; 6,171,849; 6,214,570; 5,451,370; 5,316,916; 5,213,965; and 5,213,964. By contrast, it has been found that separation of non-HDLs from HDLs can be achieved in a single substantially uniform layer 565.

Further, it has been found that precipitation and separation take place in a direction that is substantially normal to the plane established by layer 565. That is, while fluid movement occurs in all directions within layer 565, there is no significant net tangential migration of fluid from one side of layer 565 to the other. Indeed, quite unlike the prior art noted above, the present invention does not incorporate or rely on different migration rates of plasma and precipitated non-HDLs across layer 565. This is because fluid transport is through layer 565, not across it. Therefore, this may be referred to as a vertical flow system with uniform horizontal flow.

Many suitable materials can be used for layer 565, such as filter paper or cellulose acetate in combination with glass fibers. Many examples of suitable layers are provided in U.S. Pat. No. 7,087,397. One suitable membrane for layer 94 is CytoSep®™, grade 1660 membrane, 12.9 mils thick, available from Pall Corporation, East Hill, N.Y. Another suitable membrane for layer 94 is paper grade 595, 0.180 mm (7.1 mil) thick, available from Schleicher & Schuell Biosciences, Inc., Keene, N.H. Further, layer 94 is substantially uniform throughout or symmetric. That is, while the matrix of layer 565 includes pores of different sizes, the matrix is consistent throughout the entire layer. Layer 565 is impregnated with the solution described hereinbelow in the examples. Further reference is made to U.S. Pat. No. 7,087, 397.

In one embodiment, a solution for impregnation of HDL Fractionation Membrane (layer 565):

The following impregnation solution was used:
1. Deionized water 800.00 mL;
2. Magnesium Sulfate 5.00 gm;
3. Phosphotungstic Acid 45.00 gm;
4. Sorbitol 10.00 gm;
5. Adjust pH with NaOH or HCl pH 6.40-6.60; and
6. Adjust the volume to 1 liter with deionized water.

A synthetic fiber composite media (Pall CytoSep™ grade 1660) 12.9 (mils) thick, 5.90" (inches) wide, was submersed in a re-circulating bath of impregnation solution at a rate of 0.5 ft/min. It then entered a tunnel of blowing warm air (98° to 106° Fahrenheit) and a low humidity (<5% relative humidity (RH)) to completely dry. It was then slit to 0.20" (inches) strips in preparation for assembly.

Alternatively, a synthetic fiber composite media (Pall CytoSep™ grade 1661) 7.1 (mils) thick, 6.0" (inches) wide, was submersed in a re-circulating bath of impregnation solution at a rate of 0.5 ft/min. It then entered a tunnel of blowing warm air (98° to 106° Fahrenheit) and a low humidity (<5% RH) to completely dry. It was then slit to 0.20" (inches) strips in preparation for assembly.

Alternatively, a general purpose paper (Schleicher & Schuell 595) 6.0" (inches) wide was submersed in a re-circulating bath of impregnation solution at a rate of 0.5 ft/min. It then entered a tunnel of blowing warm air (98° to 106° Fahrenheit) and a low humidity (<5% RH) to completely dry. It was then slit to 0.20" (inches) strips in preparation for assembly.

Total Cholesterol Measurement Stack

With further reference to FIG. 5, stack 525 is spaced from stack 520 and is adjacent to and in fluid communication with distribution layer 515. Stack 525 takes fluid from distribution layer 515 and produces hydrogen peroxide in proportion to the concentration of total cholesterol in sample 510. Stack 525 also includes a blank or spacer layer 565 whose main purpose is to maintain the relative thickness of all stacks approximately the same and, in so doing, improves overall compression exerted upon test strip 500 by top and bottom portions of the test strip holder. Blank layer 565 also retains residual blood cells passed to it from layer 515. For purposes of this specification, the term "blank layer" refers to a layer such as layer 565 whose main purpose is to maintain all stacks at substantially the same thickness. Blank layer 565 is not loaded with any reagents but may be impregnated with a wetting agent to improve fluid flow. The function of the total cholesterol stack is according to the reaction described above in relation to FIG. 2.

Triglycerides Stack

With further reference to FIG. 5, stack 530 is spaced from stack 525 and is adjacent to and in fluid communication with layer 515. Stack 530 takes plasma from layer 515 and produces hydrogen peroxide in proportion to the concentration of total cholesterol in sample 510. Stack 530 also includes a blank or spacer layer that in this embodiment is the same as blank layer 565. Mechanisms for separating triglycerides for measurement may be found in co-owned U.S. Pat. No. 7,214,504 which is hereby incorporated by reference. Lipoprotein lipase (LPL) may be used to convert triglycerides according to the following reaction:

This reaction yields hydrogen peroxide proportional to the amount of triglycerides in the sample, which then may be electrochemically analyzed. Numerous other methodologies are available for converting triglycerides to hydrogen peroxide.

It should be understood that once HDL concentration, total cholesterol, and triglyceride concentrations are determined from stacks 520, 525, 530, respectively, the concentration of LDL cholesterol can be calculated by the well-known relationship:

LDL cholesterol=total cholesterol-triglycerides/5-HDL cholesterol

A simple linear equation like that above can easily be programmed into the instrument that reads the test strips, thus providing concentration of an additional analyte that was not measured directly.

Thus, it can now be appreciated that a single test matrix 500 as just described can be configured to test concentrations of multiple analytes.

Furthermore, the test strips described above may include one or more windows in the bottom of the test strip for optical analysis of the fluid sample. The optical analysis window may be located separate from the electrodes or in the same vertical path as the electrodes. In either case, this arrangement may allow for concurrent electrochemical and optical (reflectance) measurements to be taken.

In the embodiments described above, the test strip may have a variety of electrochemical or photometric testing sites. These sites may be combined or separated by virtue of a transparent base layer for the electrodes. Further, the testing methods may occur simultaneously or approximately so. Furthermore, since providing multiple tests is possible in a single test strip, redundancy may be built into the test strip in order to improve accuracy. This redundancy may be in the form of multiple tests for the same analyte using the same technique, preferably electrochemical. The redundancy may include testing for the same analyte according to different techniques: electrochemical and optical. Furthermore, two electrochemical tests may be done with different concentrations of reagents and analyzed according to different calibration curves. By using multiple tests of the same type or slightly modified tests, errors in testing can be more easily detected and retesting performed if necessary. Although redundancy can be incorporated in the testing of any analyte, in the case of glucose, testing errors can have serious consequences, so such redundancy may be highly desirable.

Figure 6:
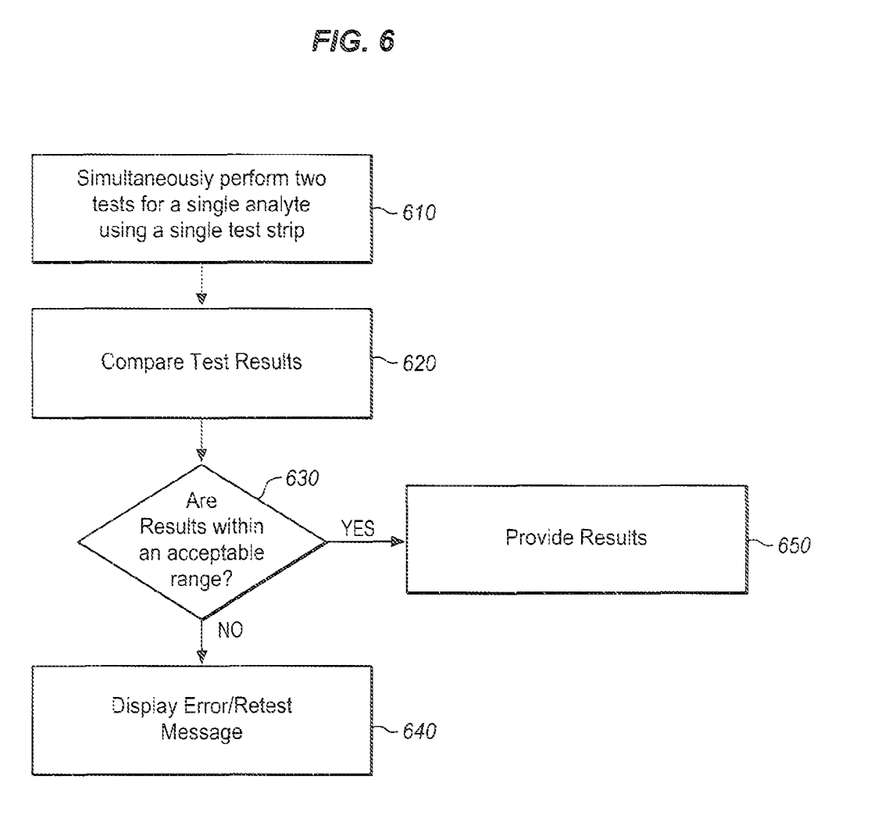
FIG. 6 is a flow chart for an embodiment of a method for ensuring accuracy of analyte testing.

FIG. 6 shows a method of providing a notification to a user upon a test result that falls outside of an acceptable error range. In block 610, two tests for a single analyte are performed simultaneously using a single test strip. In block 620, the results of the tests are compared. In block 630, if the results of the comparison are within an acceptable error range, then the flow proceeds to block 650 and the results of the test are returned to the user. If the error range is not acceptable, then the user is notified of the potential testing error, at which point one or more of the results may be returned. Further, the user may be notified that retesting is needed. This method may be programmed into the test device used in conjunction with the test strip. As described in the preceding paragraph, the two tests performed may be the same or different in terms of the methodology or reactant concentration and calibration curve.

Figure 7:
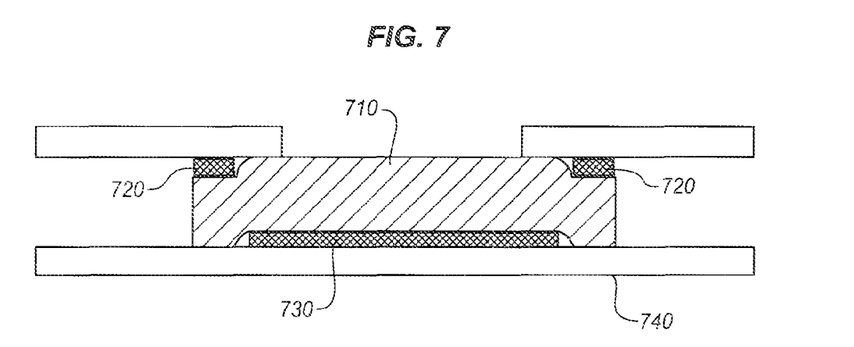
FIG. 7 shows a reaction layer with electrodes.
Figure 8:
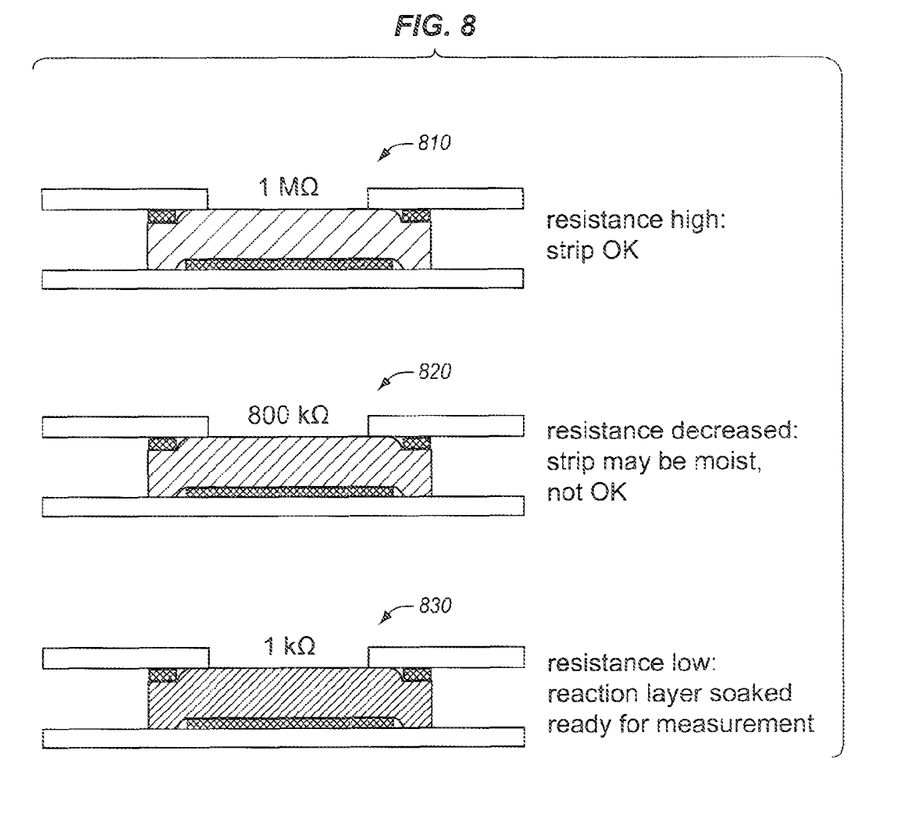
FIG. 8 shows the various resistance of test strips.

FIG. 7 shows a reaction layer 710 with an upper electrode 720 (a circular electrode shown as cross sectioned), a lower electrode 730, and a printed circuit board 740. The resistance of the reaction layer 710 changes when it is soaked with a sample. Having the reaction layer 710 enclosed between the lower and the upper electrodes 730, 720, it is possible to measure the electrical resistance of the reaction layer 710. To avoid electrolysis which might affect the measurement, a low alternating voltage can be applied for a short period of time to measure the layer's resistance. As shown in FIG. 8, a strip 810 that has been stored under dry conditions (in a closed vial) and not been exposed to air humidity should have a very high resistance (e.g., 1 M$\Omega$). If a strip 820 has been exposed to humidity and the reaction layer has become moist (it is hygroscopic because of the chemical components it has been impregnated with), the resistance would drop a bit, e.g., to 800 k$\Omega$, as in the drawing. The moisture might lead to deterioration of the enzyme function and thereby turn the strip useless, so the device would be capable of doing a pre-test functionality check. In this case, by using the moisture level of the strip as determined by the resistance before the application of the sample, a device could determine whether the strip is functional.

As soon as the sample has been applied, migrated through the layers, and started soaking the reaction layer, the resistance in a strip 830 will drop to a relatively low value (for example 1 k$\Omega$). The resistance will eventually reach a lower limit (within seconds). As the resistance does not drop further, the device "knows" that the test measurement can commence and switch to measuring the current between the working electrode and the counter-electrode.

In one embodiment, the instrument electronics are programmed to make an additional measurement between the outer electrodes of the two most distant biosensor cells. This value can be used to calculate a "baseline" that is subtracted from the individual cell values to correct for cross-talk. For instance, referring to FIG. 1, two resistance readings may be taken between the inner electrode 165 of test site 140 and the outer electrodes of test sites 145, 150. The same process may be repeated for each of the test sites, 140, 145, 150 and each set of readings is used to calculate the baseline for the respective test site. Alternatively, additional electrodes are included and used in the calculation of cross talk. Alternatively, instead of resistance being measured, a voltage measurement may be used.

The foregoing description of the embodiments of the Diagnostic Multi-Layer Dry Phase Test Strip With Integrated Biosensors and methods related thereto has been presented only for the purpose of illustration and description and is not intended to be exhaustive or to limit the Diagnostic Multi-Layer Dry Phase Test Strip With Integrated Biosensors and methods related thereto to the precise forms disclosed. Numerous modifications and adaptations are apparent to those skilled in the art without departing from the spirit and scope of the Diagnostic Multi-Layer Dry Phase Test Strip With Integrated Biosensors and methods related thereto.

The invention claimed is:

1. A diagnostic multi-layer dry phase test strip with integrated biosensors for use in measuring more than one analyte in a fluid sample, said test strip comprising:
    (a) a body having a port for introducing a fluid sample;
    (b) a spreader layer configured to evenly spread the fluid sample received through the port;
    (c) more than one enzyme reaction layer in fluidic communication with the spreader layer;
    (d) a first electrode layer in fluidic communication with the more than one enzyme reaction layer, the first electrode layer including at least one electrode for each of the more than one enzyme reaction layer, each of the at least one electrode capable of electrically interacting with the fluid sample, each of the at least one electrode being a counter-electrode, the first electrode layer located on top of the more than one enzyme layer;
    (e) an electrically insulating base layer;
    (f) a plurality of lead terminals formed on the electrically insulating base layer; and
    (g) a second electrode layer, located under the more than one enzyme layer, the second electrode layer in fluidic communication with the more than one enzyme reaction layer, the second electrode layer including at least one reference electrode and at least one working electrode for each of the more than one enzyme reaction layer, each of the at least one reference electrode and at least one working electrode capable of electrically interacting with the fluid sample.

2. The diagnostic multi-layer dry phase test strip as set forth in claim 1 wherein an electrically conducting surface of the first electrode layer is facing downward and is in fluidic communication with said more than one enzyme reaction layer.

3. The diagnostic multi-layer dry phase test strip as set forth in claim 1 wherein the electrically conducting surface of the second electrode layer is facing upward and is in fluidic communication with said more than one enzyme reaction layer.

4. The diagnostic multi-layer dry phase test strip as set forth in claim 1 wherein the first electrode layer has at least one opening.

5. The diagnostic multi-layer dry phase test strip as set forth in claim 4 wherein at least one opening is at least two openings and the at least two openings are approximately centered in the at least one working electrode and the at least one reference electrode of the second electrode layer.

6. The diagnostic multi-layer dry phase test strip as set forth in claim 5 wherein the at least one working electrode and the at least one reference electrode of the second electrode layer are circular.

7. The diagnostic multi-layer dry phase test strip as set forth in claim 1 wherein at least one additional functional layer is formed between the more than one enzyme reaction layer and the spreader layer.

8. The diagnostic multi-layer dry phase test strip as set forth in claim 7 wherein the additional functional layer is a blood separation layer.

9. The diagnostic multi-layer dry phase test strip as set forth in claim 7 wherein the additional functional layer is a precipitation layer.

10. The diagnostic multi-layer dry phase test strip as set forth in claim 7 wherein the additional layer is a spacer layer.

11. The diagnostic multi-layer dry phase test strip as set forth in claim 1 wherein a carrier base has at least one window enabling the test strip to be optically observed.

12. The diagnostic multi-layer dry phase test strip as set forth in claim 11 wherein the at least one window is opposite the port.

13. The diagnostic multi-layer dry phase test strip as set forth in claim 1 wherein said electrically insulating base layer is transparent.

14. The diagnostic multi-layer dry phase test strip as set forth in claim 1 wherein the more than one enzyme reaction layer contains chemicals for an electrochemical quantification of an enzyme reaction.

15. The diagnostic multi-layer dry phase test strip as set forth in claim 14 wherein the more than one enzyme reaction layer contains chemicals for an electrochemical and an optical quantification of the enzyme reaction.

16. The diagnostic multi-layer dry phase test strip as set forth in claim 15 wherein the electrochemical and the optical quantification occur simultaneously.

17. The diagnostic multi-layer dry phase test strip as set forth in claim 1 wherein a mediator is used.

18. The diagnostic multi-layer dry phase test strip as set forth in claim 17 wherein the mediator used is ferrocene ($Fe(C_5H_5)_2$).

19. The diagnostic multi-layer dry phase test strip as set forth in claim 17 wherein the mediator used is a ruthenium complex.

20. A diagnostic multi-layer dry phase test strip with integrated biosensors for use in measuring more than one analyte in a fluid sample, said test strip comprising:
   (a) a body having a port for introducing a fluid sample;
   (b) a spreader layer for spreading the fluid sample received through the port;
   (c) a first electrode layer in fluidic communication with the spreader layer, the first electrode layer including at least one electrode capable of electrically interacting with the fluid sample, the at least one electrode being a counter-electrode;
   (d) more than one enzyme reaction layer in fluidic communication with the spreader layer, the first electrode layer located on top of the more than one enzyme layer;
   (e) an electrically insulating base layer;
   (f) a plurality of lead terminals formed on the electrically insulating base layer; and
   (g) a second electrode layer, located under the more than one enzyme layer, the second electrode layer in fluidic communication with the more than one enzyme reaction layer, the second electrode layer including at least one reference electrode and at least one working electrode for each of the more than one enzyme reaction layer, each of the at least one reference electrode and at least one working electrode capable of electrically interacting with the fluid sample.

* * * * *